United States Patent [19]
Shaari

[11] Patent Number: 5,843,025
[45] Date of Patent: Dec. 1, 1998

[54] BANDAGE WITH EXTERNAL ANCHOR

[76] Inventor: Christopher M. Shaari, 175 East 96th St., New York, N.Y. 10128

[21] Appl. No.: 636,834

[22] Filed: Apr. 23, 1996

Related U.S. Application Data

[63] Continuation-in-part of Ser. No. 428,887, Apr. 25, 1995, abandoned.

[51] Int. Cl.$^6$ .................................................. A61F 13/00
[52] U.S. Cl. ............................. 602/53; 602/79; 607/215
[58] Field of Search ................................ 602/41–57, 79; 606/213–216

[56] References Cited

U.S. PATENT DOCUMENTS

| | | | |
|---|---|---|---|
| 1,969,188 | 8/1934 | Spicer | 607/215 |
| 3,417,749 | 12/1968 | Bailey | 602/79 X |
| 3,520,306 | 7/1970 | Gardner et al. | 607/215 |
| 3,863,640 | 2/1975 | Haverstock . | |
| 4,181,127 | 1/1980 | Linksy et al. | 607/215 |
| 4,207,885 | 6/1980 | Hampton . | |
| 4,263,906 | 4/1981 | Finley | 607/215 |
| 4,732,146 | 3/1988 | Fasline et al. | 602/79 |
| 5,133,340 | 7/1992 | Koopmann | 602/19 |
| 5,234,462 | 8/1993 | Pavletic | 606/215 |
| 5,423,736 | 6/1995 | Cartmell et al. | 602/45 |

FOREIGN PATENT DOCUMENTS

| | | | |
|---|---|---|---|
| 2268504 | 12/1975 | France | 606/215 |

OTHER PUBLICATIONS

Vijayan, N. Headache, 1993, 33:40–412.
Erwin et al., Arch. Phys. Med. Rehabil., 1991, 72:701–702.
Ehlers et al., Investigative Opthalmology & Visual Science 31, 1990, 11:2389–2394.
Wittmann et al., World J. Surg., 1990, 14:218–226.
Berardo et al., Anesth. Prog., 1989, 35:26–27.
Shaefel et al., Vision Res. 28, 5:639–657.

*Primary Examiner*—Jerome W. Donnelly
*Assistant Examiner*—Kim Lee

[57] ABSTRACT

The invention is directed to a novel bandage construction in which a dressing is held in place over a wound by means of one or more external arms capable of releasably attaching to an anchor that remains adhered to the skin. Subsequent dressing changes may be accomplished by detaching the arm and anchor mechanism, replacing the dressing, and reattaching the arm to the anchor so that the patient does not require repeated procedures adhering the dressing to the skin. The bandage design minimizes irritation and discomfort to the patient and is convenient for repeated dressing changes.

10 Claims, 12 Drawing Sheets

BANDAGE WITH EXTERNAL ANCHOR

SPECIFICATION

This application is a continuation-in-part of U.S. patent application Ser. No. 08/428,887, filed Apr. 25, 1995 now abandoned.

INTRODUCTION

The invention is directed to a novel bandage construction in which a dressing is retained in place on the skin by means of at least one external arm capable of releasably attaching to an anchor that remains adhered to the skin. Subsequent dressing changes may be accomplished by detaching the arm and anchor mechanism, replacing the dressing, and reattaching the arm to the anchor so that the patient does not require repeated procedures adhering the dressing to the skin. The bandage design minimizes irritation and discomfort to the patient and is convenient for repeated dressing changes.

BACKGROUND OF THE INVENTION

Wound management is critical to the prompt and permanent repair of injured tissues. Openings in the skin which must be covered include cuts, abrasions, lacerations, gashes, and incisions. Infections such as abscesses and boils often require covering as they are treated and resolved. Wounds in the skin may be present following injury, or alternatively, following a medical procedure such as surgery.

Application of a dressing to a wound site serves several purposes: (a) protection from physical damage and infectious agents; (b) absorption of draining fluids and retention of therapeutic ointments; (c) immobilization and (d) compression (Emergency Medicine, May, L., ed., John Wiley and Sons, New York, 1984). The dressing should insure that these purposes are met so that healing proceeds rapidly. This is typically accomplished by choosing a dressing that completely covers the wound and is properly secured to the adjacent skin, forming a bandage. The covering must be sterile and anchored close enough to the wound so that it acts as a barrier to infectious agents. The efficacy of topical agents, such as antibacterial ointments, that may be applied to the wound is dependent on dressing compression for absorption into the wound site. Furthermore, proximity and compression of the dressing over the wound opening insures maximal absorption of draining fluids.

A dressing should remain securely in place, so that the separated skin edges remain in alignment while tissue repair occurs. This requirement is particularly difficult to meet in anatomic sites where motion normally occurs, such as a joint or limb.

In a common bandage design, a wound dressing is secured with adhesive tape that is affixed to the dressing and adhered to the patient's skin. Depending on the site of the wound, the amount of tape that must be used varies. For example, head and neck wounds are located in anatomically difficult sites, and adequate securing of the dressing may require large amounts of tape. In sites where motion is present, extra tape may be required to prevent dislodging of the dressing. Where the skin is not optimally suited for tape application, i.e., oily skin or bearded skin, the ability to secure a dressing with tape is compromised.

In order to speed healing of the wound, prevent infection, and absorb drainage fluids, optimal treatment requires frequent changes of dressing. Where a dressing has been secured with tape, these changes necessitate the removal of the tape from the adjacent skin, often creating discomfort and pain for the patient. Tape is then reapplied to the same site to secure a new dressing. The frequent dressing changes require the patient to suffer the stripping of the tape from the skin each time. The irritation caused to skin from repeated tape removal may also cause erythema around the wound site, which may be confused with cell-ulitis. Optimal treatment for wound healing may dictate that a dressing is changed from 1–3 times daily, and the patient may experience a significant amount of discomfort from the treatment procedure in addition to pain that may emanate from the wound itself. In sites where the skin is covered with hair, i.e., a facial beard, further discomfort ensues from each tape removal. Where large amounts of tape have been necessary to secure the dressing, the discomfort may be severe. In fact, certain patients may require sedation in order to endure the dressing procedure. Residual material from the previous tape application may need to be removed in order to permit the attachment of new tape to the same area of skin. This residue buildup is problematic, in that subsequent tape applications may not adhere as tightly. Poor adherence may result in loose-fitting dressings that may invite infection.

Therefore, the need exists for improved methods of securing dressings to the skin that avoid discomfort to the patient. Improvements that make dressing changes less painful and more convenient make it more likely that a patient can apply a fresh dressing without medical assistance. This would be particularly advantageous in outpatient surgical procedures, where the patient is responsible for dressing changes at home. Patient compliance with medical treatment may be increased by the availability of bandage designs that facilitate the ease of dressing changes. As a result, wound management may be optimized so that healing proceeds rapidly.

SUMMARY OF THE INVENTION

The invention is directed to a novel bandage construction, in which a dressing is releasably retained in position by means of at least one external arm and at least one external anchor. One or more arms that straddle or extend from the dressing releasably attach to an anchor which is secured to the patient's skin. The anchor is initially applied to the skin, and remains adhered to the skin through repeated changes of dressing. As a result, the patient is spared the discomfort of repeated tape removal encountered in conventional dressing applications. Frequent dressing changes may be accomplished without repeated attachment or removal of any device directly from the patient's skin. The bandage affords improved convenience to the patient and healthcare worker, as it may be changed rapidly with minimal patient discomfort.

DETAILED DESCRIPTION OF THE INVENTION

The invention is directed to a novel bandage construction that is releasably retained in position by means of an external anchoring device that is itself adhered to the skin of a patient. Removal and reapplication of a dressing is accomplished through the use of a detachable anchoring mechanism, so that a patient does not undergo repeated adhesive procedures to the skin.

The bandage of the invention comprises a dressing, an arm or arms which may extend from the dressing itself or may be comprised in one or more separate elements, and an anchor that is adhered to the skin wherein the arm or arms may be releasably attached to the anchor.

A dressing is defined as any article which covers or protects any site on the body. The dressing may be made of gauze or any suitable absorbent or protective material, including but not limited to Telfa™, cotton combine, plastic, rubber, or any material that covers a site on the body. The dressing may be made of a material which is sufficiently rigid to allow at least a portion of the dressing to maintain a desired conformation without additional support; for example, such that at least a portion of the dressing retains a dome-shape over the site of application (as in, for example, an eye patch or a patch for covering an ear or chin, or a conical structure to place over a finger). Medicaments may optionally be incorporated into the body of the dressing.

The dressing may be retained in place by means of one or more coextensive arms that extend outward from the dressing and attach to the anchor, or alternatively, by means of one or more external straps that straddle the dressing and contain arms which attach to the anchor. Alternatively, a patch sized to overlie the dressing may comprise such arms at all or a portion of its periphery. At least a portion of one surface of each arm is covered with material capable of releasably attaching to the anchor. The term "releasably," as used herein, indicates that an arm may be first attached to the anchor and then separated from the anchor without undue force and without destroying the surface of either the anchor or the arm so as to preclude reattachment. Where an external strap is used, the strap may optionally further comprise an adhesive surface that binds to the dressing itself.

In another embodiment of the invention, the dressing may be directly attached to the anchor by means of an adherent surface on the underside edge of the dressing that is capable of adherence to the anchor. For example, a gauze dressing may be itself attached to an anchor comprising a hook-bearing surface (see infra).

The anchor is capable of attaching to an arm of a dressing, strap, or patch and may be adhered directly to the skin of a patient, so as to retain the dressing in the desired position. One surface of the anchor is placed in contact with the patient's skin, and another surface comprises a site capable of releasably attaching to the arm. The anchor may remain adhered to the skin through repeated changes of dressing, and preferably for the duration of wound treatment. In one nonlimiting embodiment of the invention, the anchor device consists of two parallel patches that are placed on each side of a wound. In other nonlimiting embodiments of the invention, the dimensions of the anchor are customized to a particular therapeutic application, such as when the anchor is shaped to extend along all or part of the circumference of a wound, so that a dressing may be attached to the achor via coextensive arms or so that straps may be crisscrossed across the dressing and their arms attached to the surrounding anchor to provide maximal securing of the dressing over the wound site.

The anchor may consist of a single element or more than one separate elements. The anchor may be made of any suitable durable material such as plastic, foam, rubber, or other materials that will suit the function of the invention. The anchor may be a strip of material of minimal thickness, so as to permit flexibility. The bottom surface of the strip may be adhered to the skin of a patient while the upper surface comprises an area capable of attaching to an arm of a dressing, strap, or patch. Alternatively, the anchor may have a thickness such that while its lower surface may be adhered to the skin of a patient, its top surface may be elevated relative to the point of attachment of the anchor. This embodiment may be particularly useful where the anchor is to be applied to a hair-bearing area of the subject, such that the top surface of the anchor is positioned over the surface of the hair.

The anchor may be adhered to the skin (or another suitable body surface, such as a fingernail) by means of a biocompatible adhesive, such as liquid Benzoin™, Mastisol™ or others that may be applied to at least a portion of one surface of the anchor for adherence to the skin.

Alternatively, one surface of the anchor may be precoated with an adhesive that may be rendered available for adhesion upon removal of a protective strip. Where biocompatible adhesives are used, any adhesive residue left at the end of treatment may be removed with a suitable solvent (e.g. acetone). It may be desirable for the attachment of the anchor to be water tight, for example, in situations where a wound is expected to produce drainage fluid which may dissolve the adhesive used to adhere the anchor to the skin. In further embodiments of the invention, the anchor may be adhered to the skin by sutures, surgical staples or adhesive tape. Non-adhesive means for attaching the anchor (e.g., which employ sutures or staples) may be preferable when the anchor is being attached to a hair-bearing area of the subject.

In various embodiments of the invention, the anchor may be fenestrated in order to conform to the skin so as to provide flexibility and/or stretchability to the anchor in sites where motion is frequent, thus preventing detachment of the anchor by a shearing force. Such embodiments allow for placement of the bandage in such sites as the knee, elbow, wrist, face, hand and foot where secure attachment of a bandage is often compromised. Similarly, the arms which attach to the anchors may be made of flexible and/or stretchable materials.

In a particular embodiment, the anchor has an attachment site for the arm as well as one or more press sites on the edge of the anchor which may be used to hold the anchor in position while detaching the arm from the anchor. Such press sites are preferably devoid of adherent material on the upper face but contain adherent material on the lower face (which contacts the skin), thereby facilitating attachment to the skin and minimizing pulling of the skin (and hence distortion of the wound) during dressing changes. The press sites may be of equal dimension (length, width) to the anchor or they may be a size suitable for pressing while detaching the arm-anchor mechanism. In a particular embodiment, the press sites may comprise Tegaderm™ or a similar bioadhesive material which is coextensive in size with the anchor and is capable of adhering to the skin.

The press sites may also be adhered to the skin by means of sutures, surgical staples, adhesive tape, liquid Benzoin™, Mastisol™ or any other means of adherence.

The dressing may be held in place by an arm or arms that attach to the anchor. Such arm or arms may be coextensive with the dressing, or may be comprised in a strap or straps or patch that may be used to hold the dressing in position. In particular embodiments, the arm may be shaped to the circumference of the dressing so that it acts to lock and cover the dressing in place by means for attachment to an anchor that is configured to the dimension of the arm or by means of several anchors, each preferably smaller than the arm, that hold the arm in place. In preferred embodiments of the invention, the means for attachment may be a quick-locking arrangement of hook and loop cloth. Hook and loop cloth is a type of attaching means in which one member includes many little tines or hooks and another member has a fabric or fabric-like material that is gripped and held by the tines when they are brought into engagement. In such embodiments, the arm or arms and the anchor are each covered with a complementary hook or loop surface so that their cooperating means become entangled and thereby lock. In one embodiment of the invention, the hook and loop cloth may be comprised of Velcro™ or Velcro-like material. Any two surfaces which do not, when taken separately, have adhesive properties but which adhere to one another are within the scope of this disclosure. For example, a gauze dressing and the hook surface of Velcro, comprised in an anchor, may be used.

In more preferred specific embodiments, the arm may be covered with the loop-like cloth surface, while the anchor may be covered with the hook-like complementary surface. These embodiments insure that the surface that faces down toward the skin of the patient is smooth and will not irritate the skin if contact occurs. In other embodiments, the arm and anchor may be cooperatively engaged using such means as a hook and eye, ball and socket, complementary snaps, magnets or any other means that results in adherence of the arm to the anchor.

The attachment surface of an arm or anchor may comprise all or part of the available area of an arm or anchor. Preferably, the attachment surfaces of an arm or anchor are of equal size so as to avoid extraneous exposure of irritating surfaces to the skin.

It will be understood by those skilled in the art that the bandage design may be readily customized by manipulating the conformation and size of the anchor, the number of arms, the position of the arm or arms relative to the anchor, and so forth. It is possible to construct a bandage according to the invention that is maximally tight at the start of treatment by the use of several arms attached to an anchor. As treatment continues, the number of arms may be reduced to permit a looser dressing as is warranted. The placement of the arms relative to the dressing may be customized by the external placement of a patch or one or more straps, or alternatively by designing arms coextensive with the dressing to virtually any configuration desired.

For use of the bandage of the invention, one or more anchors may be adhered to the skin, the dressing may be applied to the site directly, and then the dressing may be secured in place by one or more arms by means of their attachment to one or more anchors. In this manner, frequent dressing changes may be accomplished by simply removing the dressing by detaching the arms from the anchor, applying a fresh dressing and reattaching the arms to the anchor. The advantage of this bandage design is that there is no need to strip adhesive directly from the skin with attendant discomfort to the patient.

The bandage of the present invention may have utility in any therapeutic application in which a wound requires secure protection while the injured tissues heal. The design insures secure attachment of a dressing, which aids in the absorption of fluids that may drain from the wound. Furthermore, the possibility of infection is lessened by a tight-fitting bandage that excludes foreign material while maintaining any anti-infective ointments in place. The dressing is convenient to apply and remove, and therefore requires a minimum of medical assistance. For example, when a patient has undergone an ambulatory surgical procedure, the ease of dressing changes afforded by the bandage of the invention may increase patient compliance with medical instructions regarding frequent dressing changes at home.

The bandage of the invention may be used to treat any traumatic wound or following any surgical procedure, and may be applied intra-operatively or following surgery. For example, and not by way of limitation, the bandage of the invention may be used following abdominal surgery, including such procedures as laparotomy, appendectomy, and cholecystectomy, or following surgery involving the extremities, such as tendon release. The bandage may be particularly useful in treatment of wounds in the head and neck area, including traumatic and surgical wounds associated with craniotomy, neck dissection, thyroidectomy, tracheostomy, and parotidectomy, mastoidectomy and facelift, in view of the difficult anatomic location as well as the increased sensitivity of these areas during dressing changes. For example, the bandage may function to position an eyepatch following injury or ophthalmic surgery. Facial wounds that require frequent dressing changes may be optimally treated with a bandage that does not involve repeated adhesive procedures for the patient.

It will be understood by those skilled in the art that the arm and anchor mechanism of the present invention may be used to secure any commercially available dressings, coverings, or protectors thus forming the bandage design of the invention. The arm and anchor mechanism may further be used to facilitate closure of a wound by positioning an anchor on either side of the wound and drawing the sides together by means of one or more arms that attach to each anchor and close the opening in the skin. For example, the arm and anchor device may be used to join the skin edges on the sides of an incision following a tracheostomy. In another example, an arm and anchor device may be used to promote healing in a wound allowed to heal by secondary intention.

Furthermore, in other medical conditions requiring covering of a part of the body, the arm and anchor design may be analogously employed to maintain any covering device in place on the body. For example, an arm-anchor device may be used to maintain a covering over scar tissue that requires protection, to hold an intravenous catheter in position, to secure a medical article close to a patient's body, to render structural support to a joint or tendon, or to hold a colostomy bag in place. The arm and anchor may secure an optometric eyepatch or protector, or may hold a seal over the site of a tracheostomy, or may maintain a tracheostomy "collar" in position. In medical conditions involving burns, the bandage design of the invention may minimize pain and discomfort to the patient who must keep the burn area protected.

The bandage of the present invention may be available in a kit that comprises the arm, anchor and dressing components. A kit may also comprise the arm and anchor devices for use in holding any covering device on the body. When the arm is an external strap or patch, the strap or patch may be cut to a desired length or shape from a preformed sheet or roll of arm material. A kit may contain a sheet or roll of dressing/arm material and a sheet or roll of anchor material from which both may be cut for a customized application. It may optionally contain an anti-infective ointment or spray.

The advantages of the invention will be apparent to those skilled in the art after considering this specification in view of the accompanying drawings.

Figure 1:
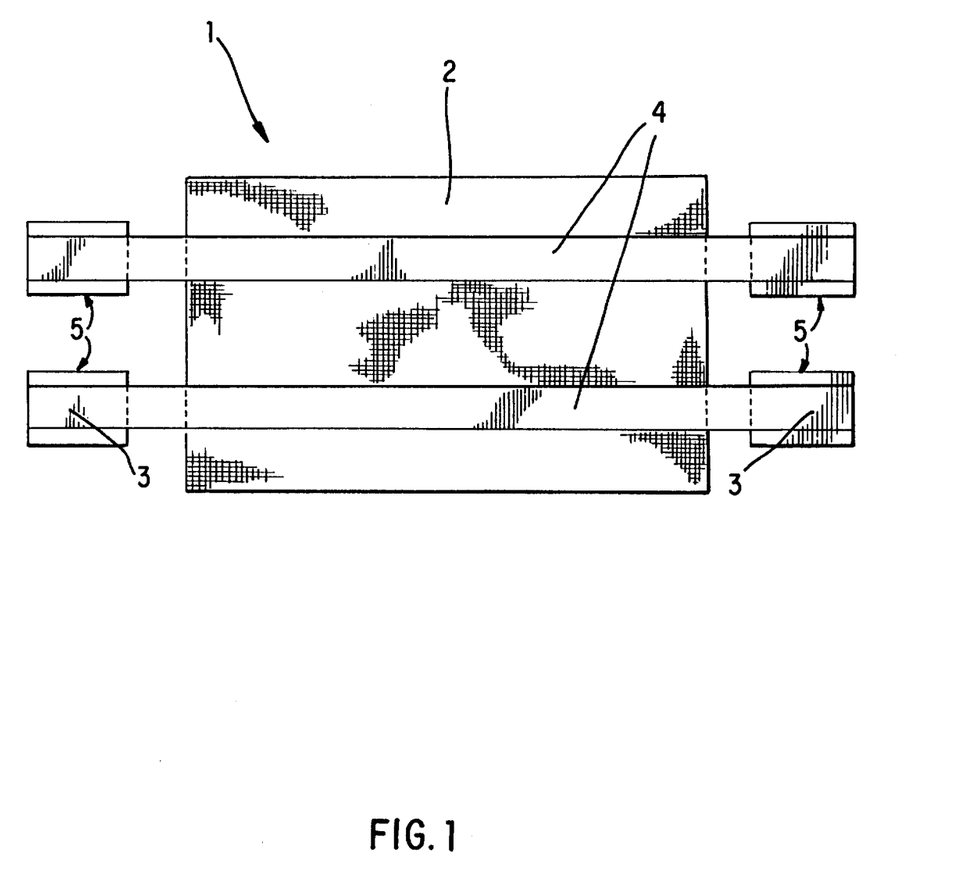
FIG. 1. Top view of a bandage of the present invention, depicting the dressing attached to the anchor by means of arms contained in external straps.

Referring to the drawings more particularly by reference numbers, FIG. 1 shows a view of an embodiment which is a bandage 1 containing a dressing 2 which is held in place by means of external arms 3 that extend from an external strap 4 and attach to anchors 5.

Figure 2:
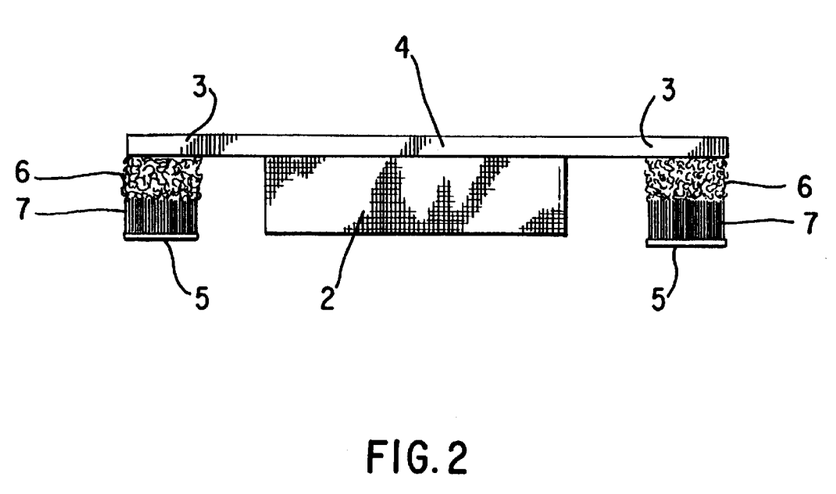
FIG. 2. Side view of a dressing retained in place by an external strap releasably attached to an anchor via arms.

FIG. 2 shows a side view of the bandage of FIG. 1, wherein external arms 3 contained in an external strap 4 attach to an anchor 5 to retain the dressing 2 in place.

Figure 3:
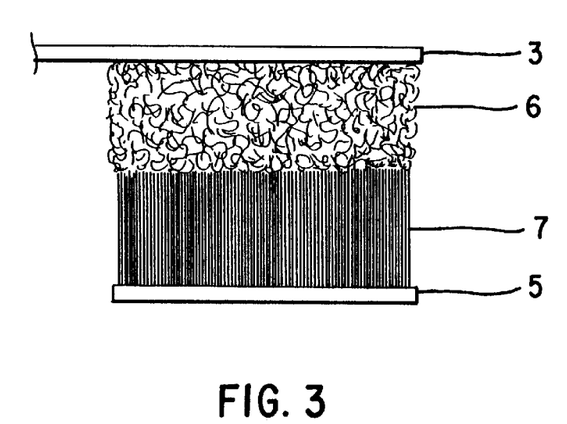
FIG. 3. Enlarged side view of an external arm attached to an anchor by means of complementary hook and loop cloth.

FIG. 3 shows an enlarged side view of the external arm 3 covered with loop cloth surface 6 attached to the hook cloth surface 7 of the anchor 5 which is adhered to the skin.

Figure 4:
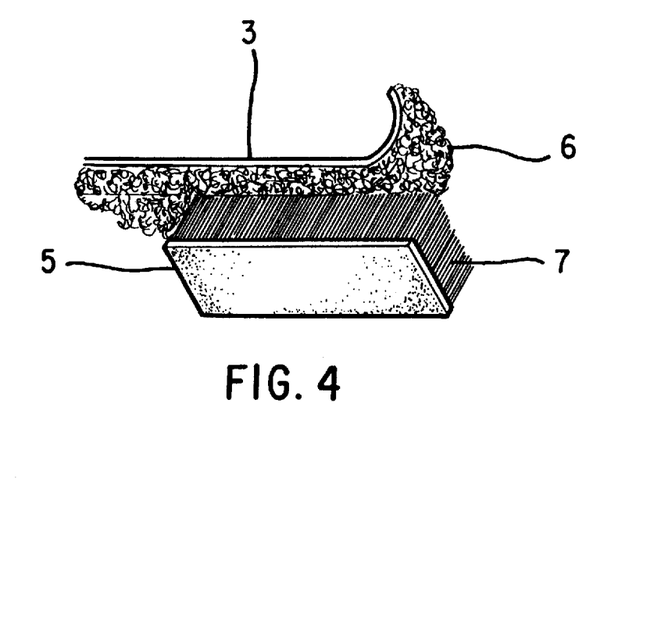
FIG. 4. View of an external arm releasably detaching from an anchor.

FIG. 4 is a view of an arm 3 which is releasably attached to anchor 5 by means of its loop cloth surface 6 that is complementary to hook cloth surface 7 on the anchor.

Figure 5:
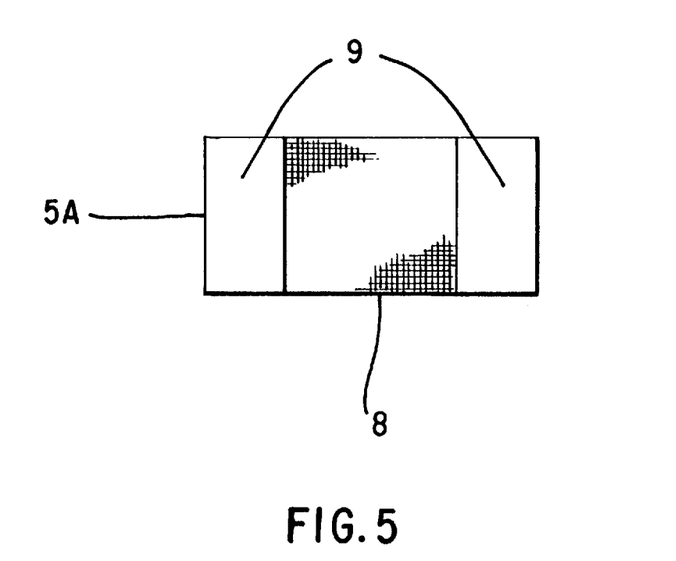
FIG. 5. Top view of an anchor containing an attachment site and press sites.

FIG. 5 shows a top view of an anchor 5A that contains an attachment site 8 and press sites 9 for use in holding the anchor while releasing a dressing.

Figure 6:
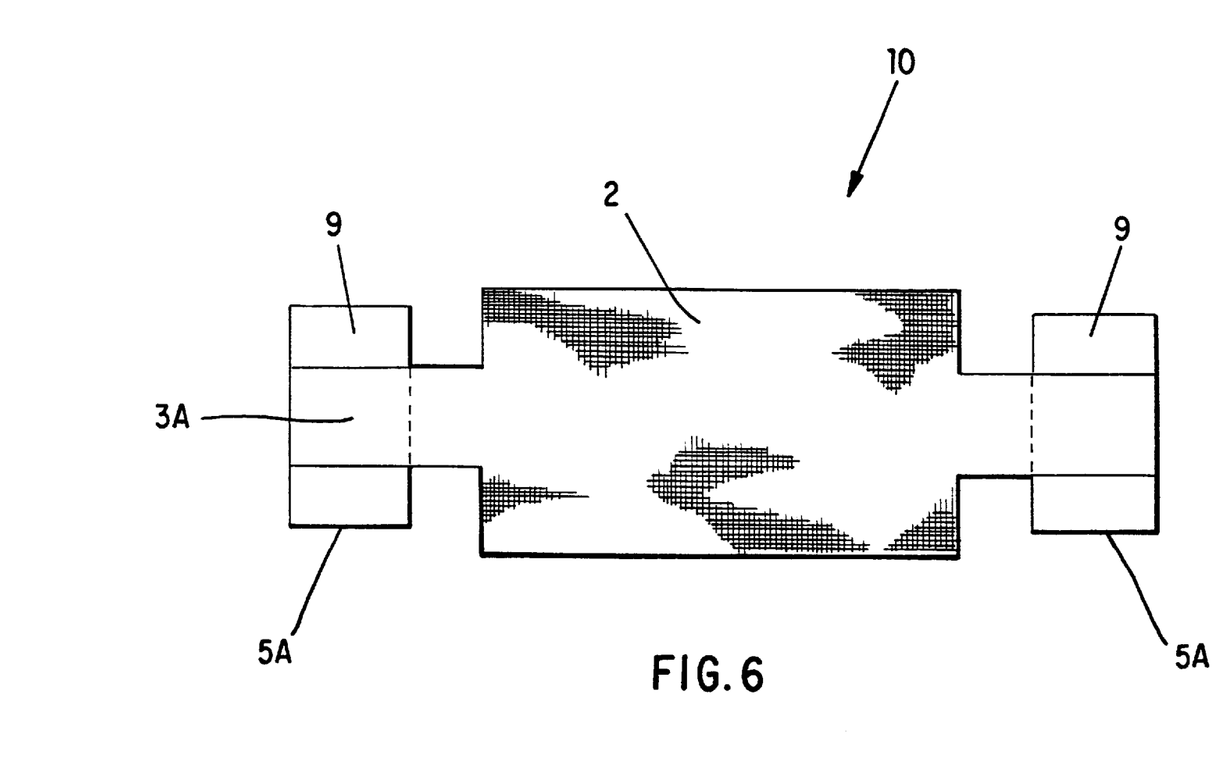
FIG. 6. Top view of a bandage of the present invention, depicting a dressing with coextensive arms attached to an anchor with press sites.

FIG. 6 shows a top view of an embodiment which is a bandage 10 that contains a dressing 2 which has coextensive arms 3A that attach to anchor 5A which contains press sites 9.

Figure 7:
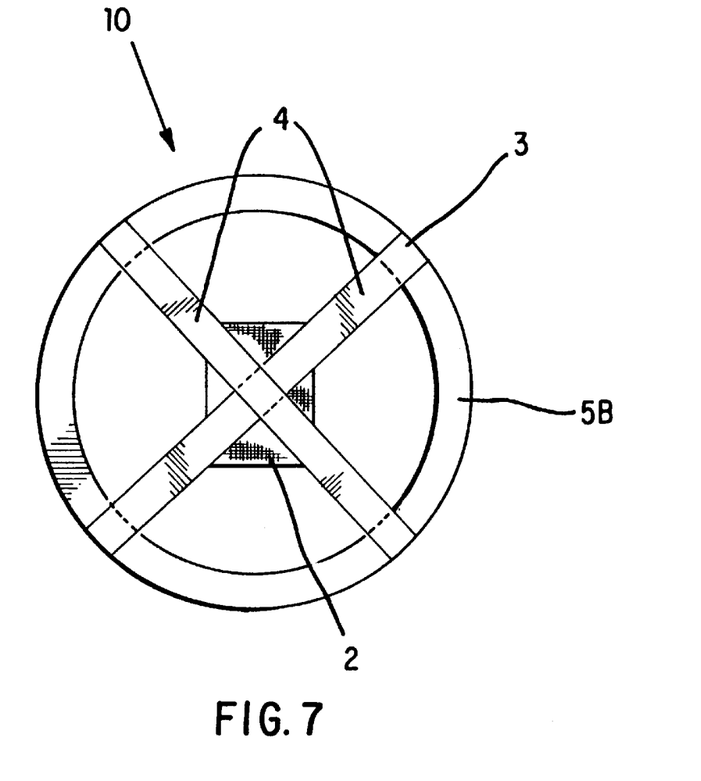
FIG. 7. Top view of a bandage of the present invention, depicting a dressing attached to an anchor sized to the circumference of a body site by means of external arms contained in external straps.

FIG. 7 shows an embodiment which is a bandage 10 that contains a dressing 2 which is retained by external straps 4 containing external arms 3 which attach to anchors 5B.

Figure 8:
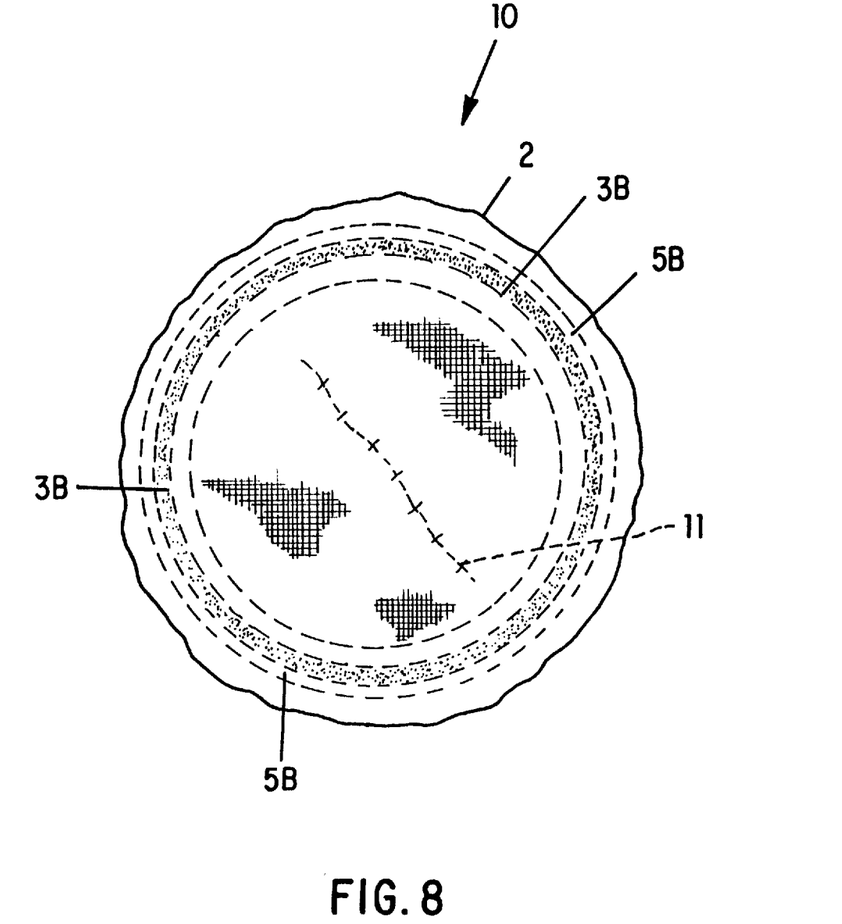
FIG. 8. Top view of a bandage of the present invention, depicting a circular dressing attached to a ring-shaped achor, overlying a wound of a subject.

FIG. 8 shows a top view of a bandage 10 that contains a circular dressing 2 attached, by means a ring-shaped coextensive arm located at the periphery of the dressing 3B (stippled area), to a ring-shaped anchor 5B, positioned over a wound 11 of a subject.

Figure 9:
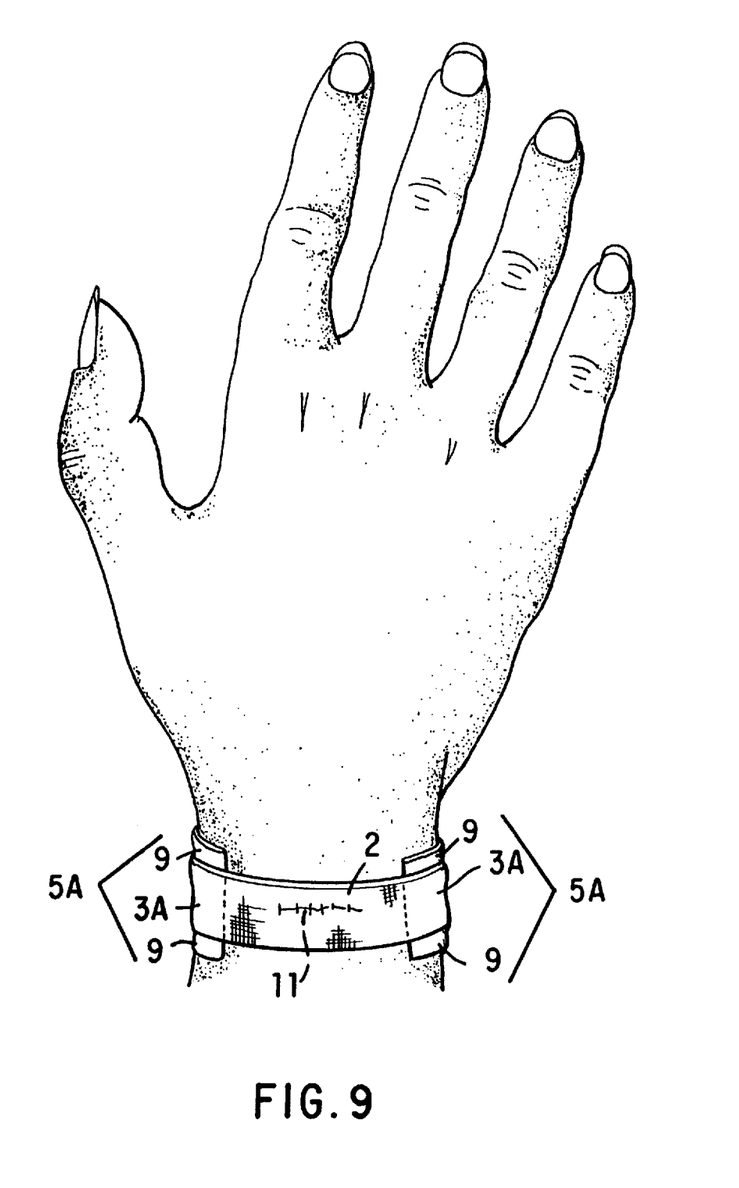
FIG. 9. Top view of a bandage of the present invention, as applied over a wound on the wrist of a subject, showing a dressing having coextensive stretchable arms which allow flexion of the wrist.

FIG. 9 shows a top view of a bandage of the present invention, as applied over a wound 11 on the wrist of a subject, showing a dressing 2 having coextensive stretchable arms 3A which allow flexion of the wrist, attached to anchors 5A having press sites 9.

Figure 10:
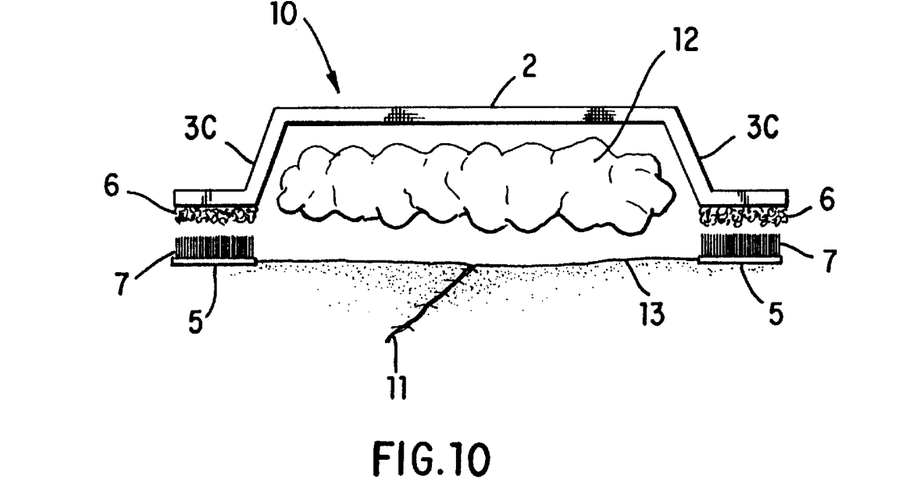
FIG. 10. Side view of a bandage of the present invention, as applied over a wound of a subject, wherein the dressing has coextensive arms which are angled relative to the portion of the dressing overlying the wound, thereby creating a space between the dressing and the wound and allowing for the positioning of a supplemental dressing over the wound.

FIG. 10 shows a side view of a bandage 10 of the present invention, as applied over a wound 11 in the skin 13 of a subject, wherein the dressing 2 has coextensive arms 3C which are angled relative to the portion of the dressing overlying the wound, thereby creating a space between the dressing 2 and the wound 11 and allowing for the positioning of a supplemental dressing 12 over the wound.

Figure 11:
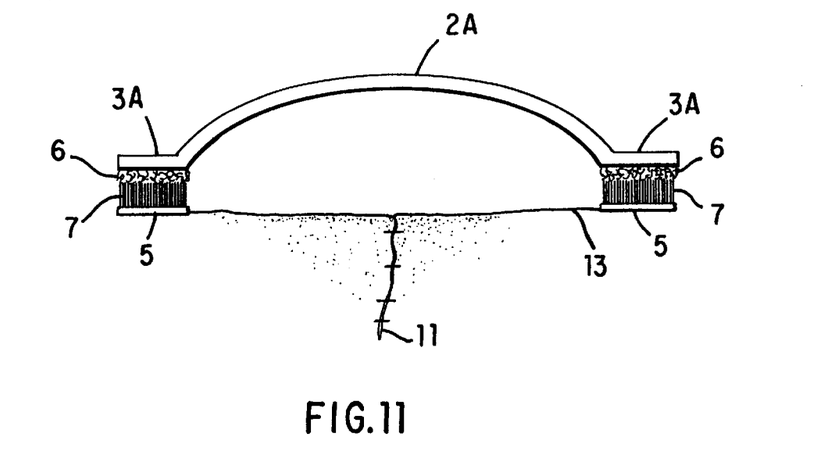
FIG. 11. Cross section of a bandage of the present invention, as applied over a wound of a subject, wherein the dressing is constructed of a material which is sufficiently rigid to allow the maintenance of a space over the wound when the bandage is affixed to a subject.

FIG. 11 shows a cross section of a bandage of the present invention, as applied over a wound 11 of a subject, wherein the dressing 2A is constructed of a material which is sufficiently rigid to allow the maintenance of a space over the wound when the bandage is affixed to a subject.

Figure 12:
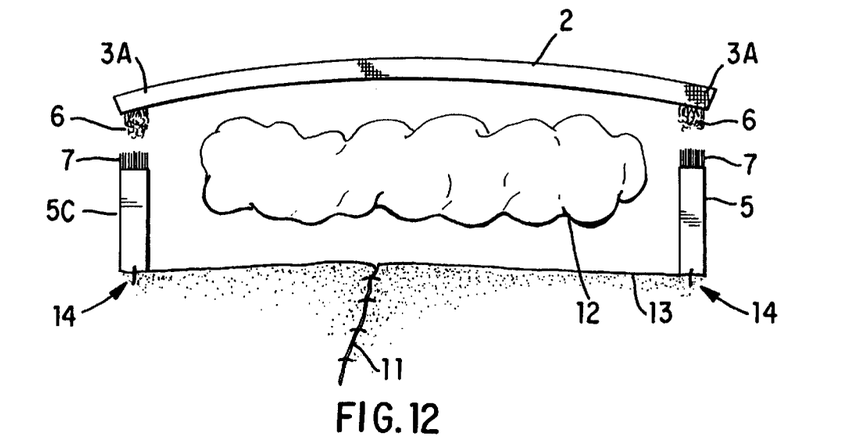
FIG. 12. Side view of a bandage of the present invention, as applied over a wound of a subject, wherein the top surfaces of the anchors are elevated such that they attach to coextensive arms of the dressing at a level above the plane of attachment of the bottom surfaces of the anchors to the subject.

FIG. 12 shows a side view of a bandage of the present invention, as applied over a wound 11 of a subject, wherein the top surfaces 7 of the anchors 5C are elevated such that they attach to coextensive arms 3A of the dressing 2 at a level above the plane of attachment of the bottom surfaces of the anchors to the subject, wherein the bottom surfaces of the anchors are adhered to the skin of the subject 13 by sutures 14.

Figure 13:
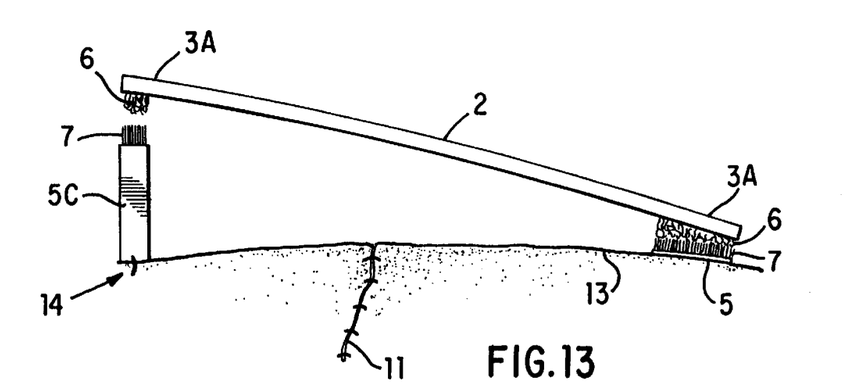
FIG. 13. Side view of a bandage of the present invention, as applied over a wound of a subject, wherein the top surface of one of the anchors is elevated above the plane of attachment of the bottom surface of said anchor to the subject.

FIG. 13 shows a side view of a bandage of the present invention, as applied over a wound 11 in the skin 13 of a subject, wherein the top surface 7 of one of the anchors 5C is elevated above the plane of attachment of the bottom surface of said anchor (adhered by suture 14) to the subject.

Figure 14:
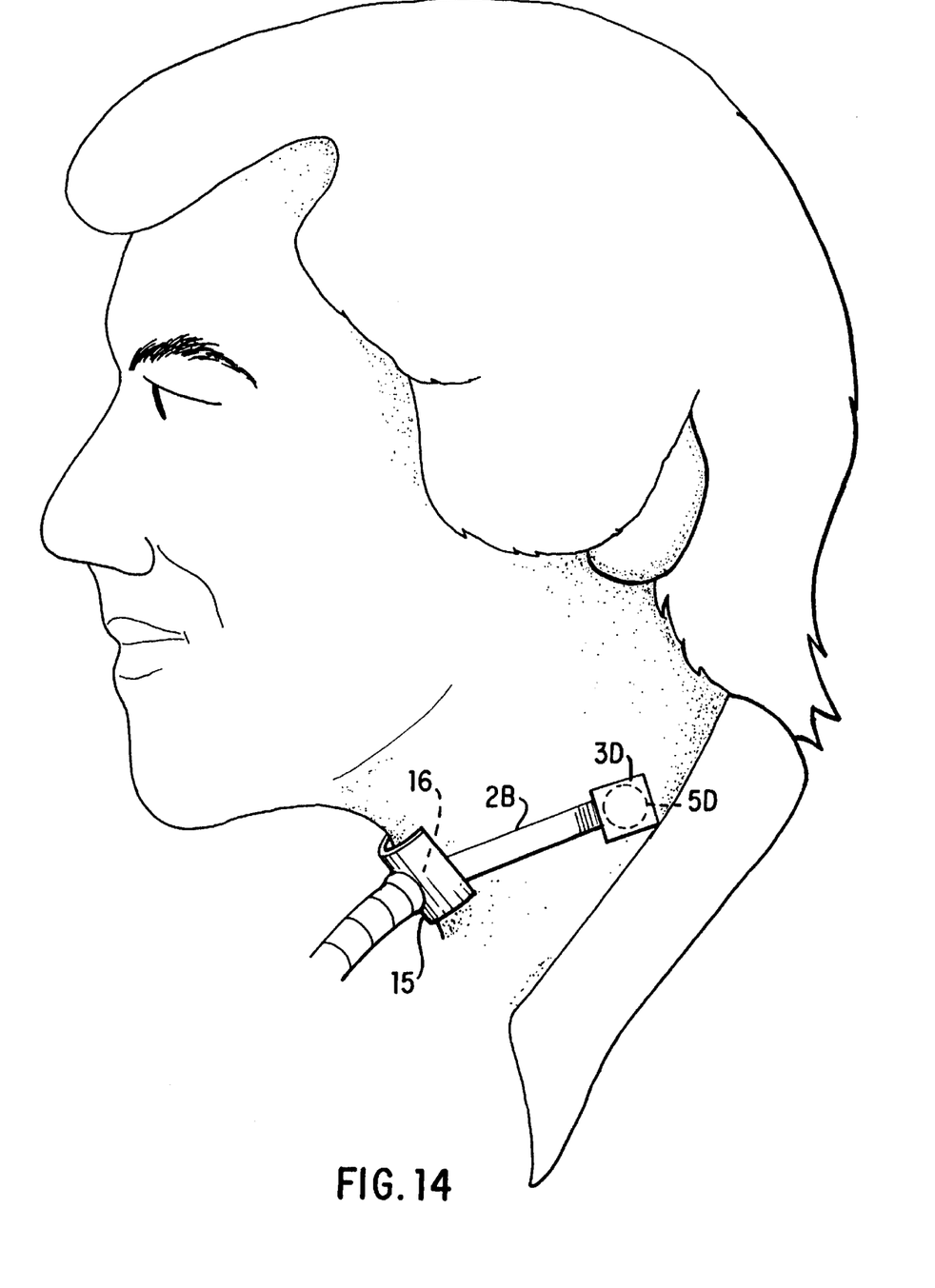
FIG. 14. Top view of a bandage of the invention, as applied to maintain a tracheostomy collar in position on a subject.

FIG. 14 shows a top lateral view of a bandage of the invention, as applied to maintain tracheostomy collar 15 in place over a tracheostomy site 16 on a subject, wherein a dressing 2B extends outward from the collar and adheres to the subject via an arm 3D that attaches to an anchor 5D located lateral to the tracheostomy site 16.

Figure 15:
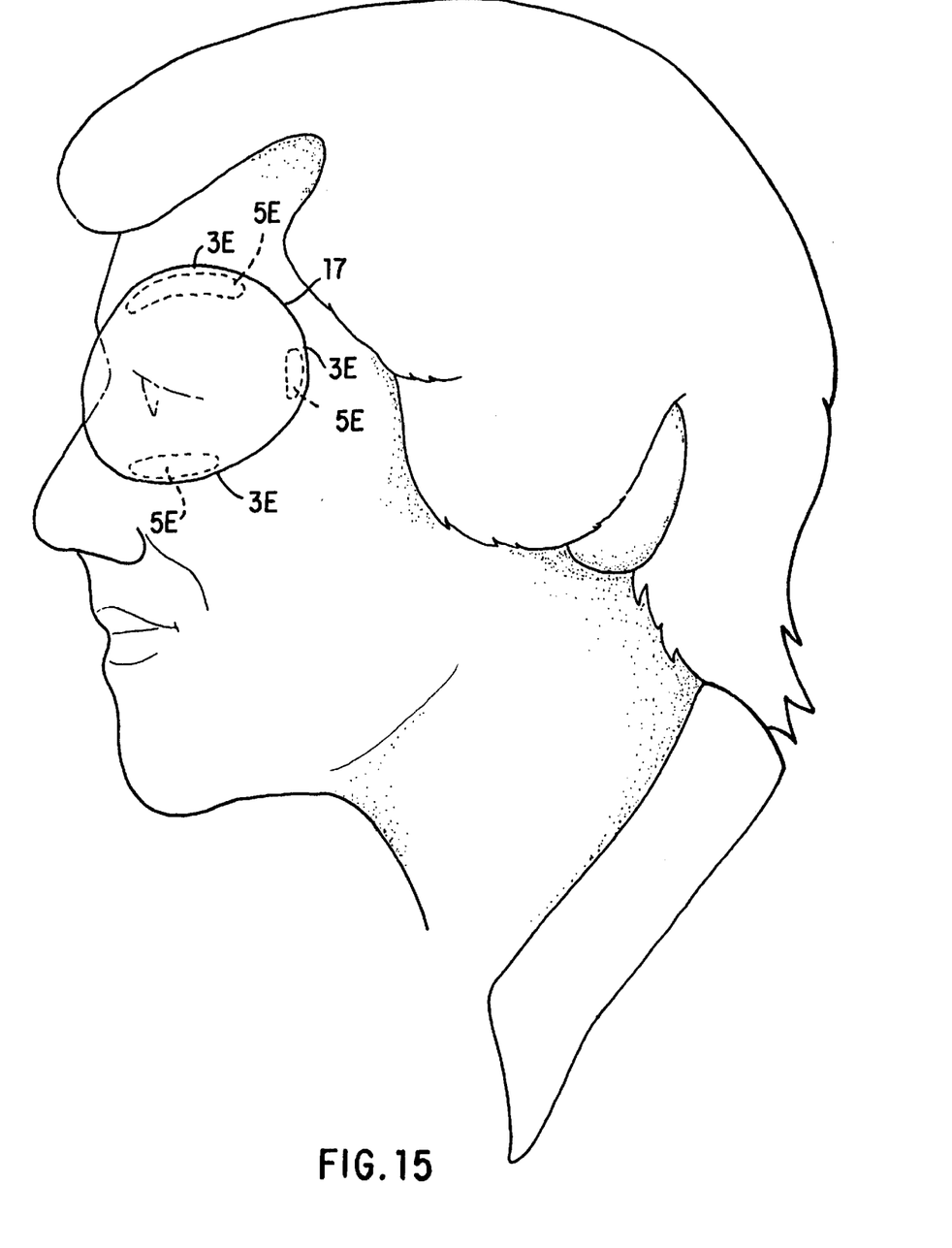
FIG. 15. Top view of an eyepatch according to the invention.

FIG. 15 shows an eyepatch 17 according to the invention, held in place over an eye of a subject by coextensive arms 3E attaching to anchors 5E.

Figure 16:
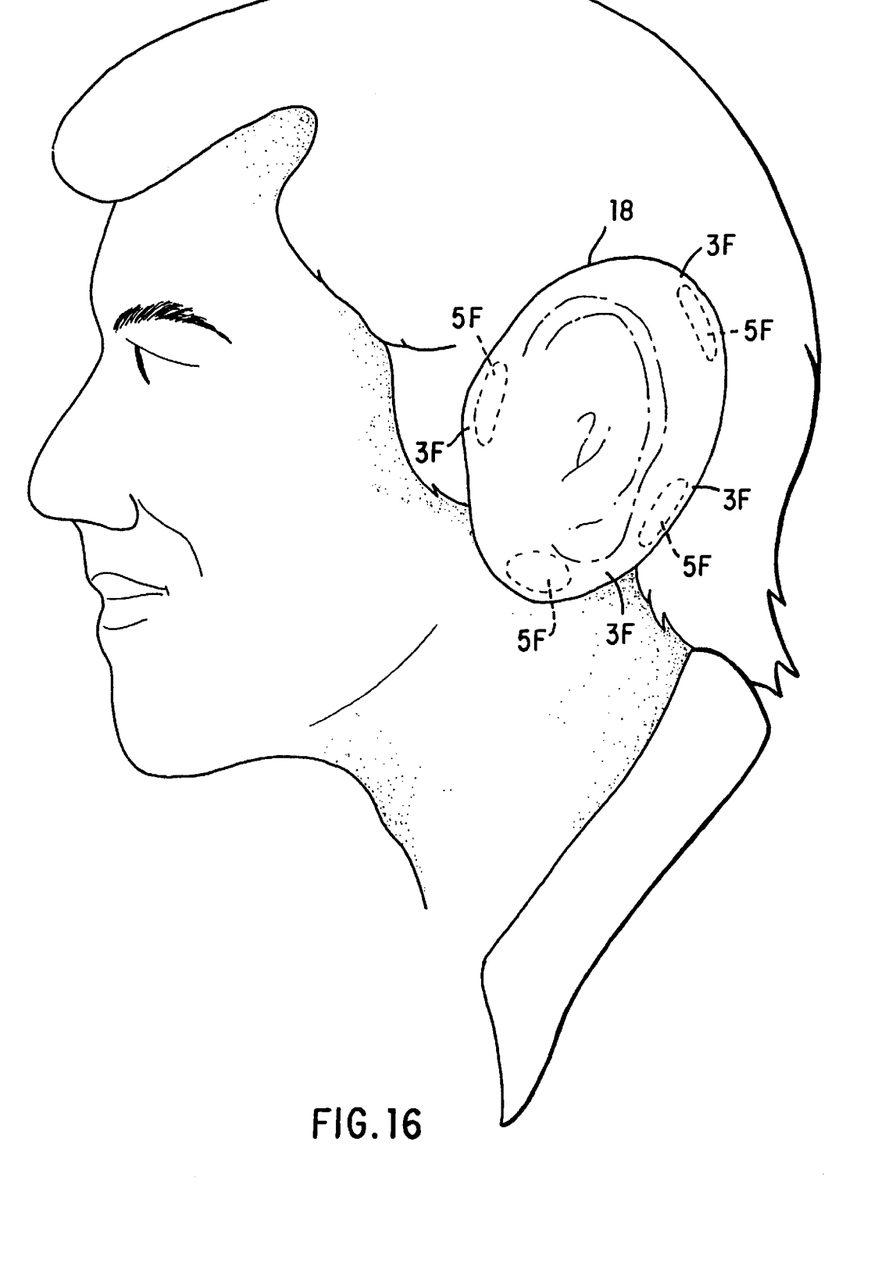
FIG. 16. Top view of an ear patch of the invention.

FIG. 16 shows an earpatch 18 according to the invention, held in place over an ear of a subject by coextensive arms 3F attaching to anchors 5F.

Figure 17:
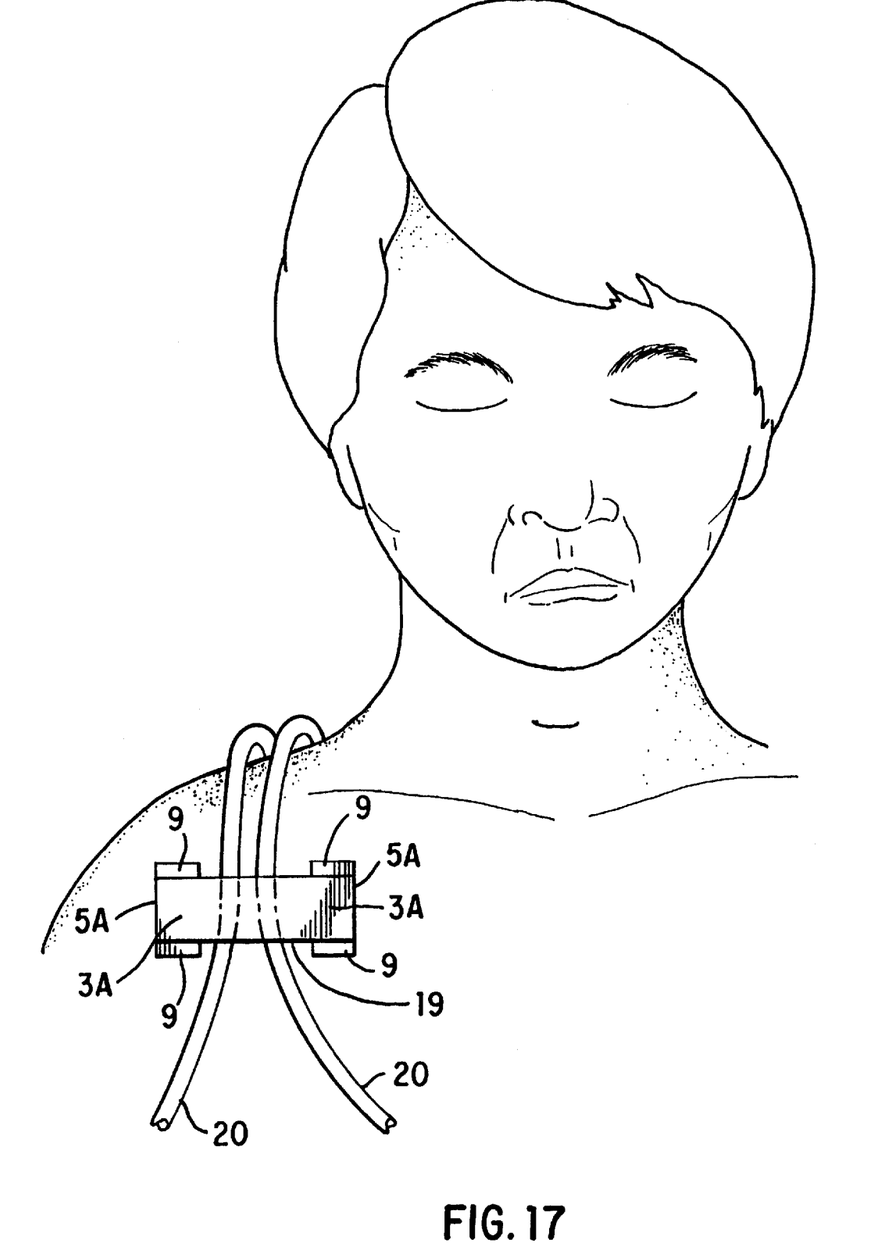
FIG. 17. Top view of a bandage of the invention holding intravenous lines in place on the shoulder of a subject.

FIG. 17 depicts a bandage 19 according to the invention which is attached to the shoulder of a subject via coextensive arms 3A and anchors 5A having press sites 9, wherein various tubings 20 may be held in place by the bandage 19.

I claim:

1. A bandage, comprising
   (a) a dressing;
   (b) at least one arm coextensive with the dressing, which is fabricated from a non-elastomeric material and capable of retaining the dressing in a desired position on the body of a subject; and, (c) an anchor having a lower surface and an upper surface, said upper surface being capable of releasably attaching to the arm and said lower surface being adapted to be adhered to the skin of the subject.

2. The bandage of claim 1, in which the dressing is a gauze dressing.

3. The bandage of claim 2, in which the means for releasably attaching the external arm to the anchor is a cooperating engagable means of the hook and loop cloth type.

4. The bandage of claim 3, in which the external arm comprises a loop-like cloth surface and the anchor comprises a hook-like cloth surface.

5. A method for providing a stable dressing to treat a wound, comprising covering the wound with the bandage of claim 2.

6. The bandage of claim 1, in which the arm is releasably attached to the upper surface of the anchor by a cooperating engageable means of the hook and loop cloth type.

7. The bandage of claim 6, in which the external arm comprises a loop-like cloth surface and the anchor comprises a hook-like cloth surface.

8. The bandage of claim 1, in which the anchor has press sites capable of holding the anchor in place during a change of dressing.

9. A method for providing a stable dressing to treat a wound, comprising covering the wound with the bandage of claim 8.

10. A method for providing a stable dressing to treat a wound, comprising covering the wound with the bandage of claim 1.

* * * * *